United States Patent
Chaligne

(10) Patent No.: US 11,607,477 B2
(45) Date of Patent: Mar. 21, 2023

(54) APPARATUS AND SYSTEM FOR REDUCING VACCUM PUMP NOISE

(71) Applicant: ZIMMER GMBH, Winterthur (CH)

(72) Inventor: Sebastien Chaligne, Brette les Pins (FR)

(73) Assignee: Zimmer GmbH, Winterthur (CH)

(*) Notice: Subject to any disclaimer, the term of this patent is extended or adjusted under 35 U.S.C. 154(b) by 0 days.

(21) Appl. No.: 17/165,187

(22) Filed: Feb. 2, 2021

(65) Prior Publication Data

US 2021/0244862 A1 Aug. 12, 2021

Related U.S. Application Data

(60) Provisional application No. 62/972,412, filed on Feb. 10, 2020.

(51) Int. Cl.
*A61M 1/00* (2006.01)

(52) U.S. Cl.
CPC ....... *A61M 1/0023* (2013.01); *A61M 2205/42* (2013.01)

(58) Field of Classification Search
CPC ...... A61M 2205/42; A61M 1/80; A61M 1/71; F04C 29/065; F04C 29/066; F04C 18/123
See application file for complete search history.

(56) References Cited

U.S. PATENT DOCUMENTS 6,543,741 B1 * 4/2003 Li ................. F04B 39/0044
248/638
2004/0163884 A1 8/2004 Austin et al.
(Continued)

FOREIGN PATENT DOCUMENTS

CA 3081132 5/2019
CN 107929831 A * 4/2018 ............. A61M 1/80
(Continued)

OTHER PUBLICATIONS https://www.collinsdictionary.com/us/dictionary/english/silencer (Year: 2022).*

(Continued)

*Primary Examiner* — Susan S Su
*Assistant Examiner* — Eric Rassavong
(74) *Attorney, Agent, or Firm* — Schwegman Lundberg & Woessner, P.A.

(57) ABSTRACT

An apparatus for applying a vacuum during a surgical procedure can include a vacuum pump assembly having a port, a first housing, a second housing, a first silencer or tubular magnet and a second silencer. The first housing can define a first cavity receiving the vacuum pump assembly therein. A portion of the first housing can be formed by a portion of the port. The second housing can define a second cavity receiving the first housing therein. A portion of the second housing can be formed by a second portion of the port. The first silencer or tubular magnet can be coupled to the first housing and can have a longitudinal extent along a longitudinal axis. The first silencer or tubular magnet can extend from the first housing within the second cavity. The second silencer can be coupled to the second housing and can have a longitudinal extent along a longitudinal axis. The second silencer can extend from the second housing within second cavity.

16 Claims, 5 Drawing Sheets

(56) References Cited

U.S. PATENT DOCUMENTS

| | | | |
|---|---|---|---|
| 2014/0161640 A1* | 6/2014 | Geue | F04C 29/066 417/312 |
| 2017/0274125 A1* | 9/2017 | Minskoff | A61M 1/743 |
| 2019/0162187 A1* | 5/2019 | Cappuzzo | F04C 29/0085 |

FOREIGN PATENT DOCUMENTS

| | | | | |
|---|---|---|---|---|
| WO | 2016103033 | 6/2016 | | |
| WO | WO-2016103033 A2 * | 6/2016 | | A61M 1/90 |
| WO | WO-2017157691 A1 * | 9/2017 | | A61M 1/04 |

OTHER PUBLICATIONS

"European Application Serial No. 21156339.0, Extended European Search Report dated Jun. 22, 2021", 9 pgs.

"European Application Serial No. 21156339.0, Response filed Feb. 11, 2022 to Extended European Search Report dated Jun. 22, 2021", 7 pgs.

* cited by examiner

APPARATUS AND SYSTEM FOR REDUCING VACCUM PUMP NOISE

CLAIMS OR PRIORITY

This application claims the benefit of U.S. Provisional Patent Application Ser. No. 62/972,412, filed on Feb. 10, 2020, the benefit of priority of which is claimed hereby, and which is incorporated by reference herein in its entirety.

FIELD

The present subject matter relates to apparatuses, systems and methods for reducing noise produced by a vacuum pump used during a medical procedure.

BACKGROUND

Vacuum pumps are used for a variety of applications during surgical and other medical procedures. For example, biological fluids and other types of medical waste often must be collected during surgery or other medical procedures. This is typically accomplished using a medical waste fluid collection cart, which may be part of a medical waste fluid collection and disposal system. Such carts may include at least one suction canister where a vacuum port on the canister lid is connected to a source of vacuum via a hose or line. As a result, a vacuum is drawn on the interior of the canister. A second hose or line is connected to a "patient" suction port on the canister lid and is used to collect medical waste in the form of fluids and solids from the patient, which is stored in the canister.

According to another example, a vacuum pump can be used during a process of making bone cement. Bone cement can be provided as a kit including a liquid monomer component and a powder initiator component, which are combined to polymerize the monomer into a sticky, dough-like paste that can be applied to a bone or an implant before hardening into cement. During mixing of the components and polymerization, bubbles can form in the viscous paste, which can cause the resulting cement to have a porous structure. The cement components can be combined and mixed under vacuum to minimize bubbles in the paste and reduce the porosity of the resulting cement. As the bone cement typically hardens within minutes of combining the components, the paste must typically be formed within the surgical suite immediately before application of the paste to the bone or implant.

OVERVIEW

This disclosure pertains generally to apparatuses, systems and methods for reducing vacuum pump noise. Although described in relation to surgical procedures, the apparatuses, systems and methods are applicable to applications where a vacuum pump is utilized and reduction in noise generated by such vacuum pump is desirable.

The apparatuses, systems and methods of the present application help reduce noise that results from operation of the vacuum pump. This reduction in noise can be of particular importance where the vacuum pump is utilized in the surgical suite as it is desirable to provide the surgeon and other personnel with a more tolerable working environment. The present apparatuses, systems and method with the vacuum pump can be utilized with various medical applications not specifically illustrated or described such as, but not limited to, a medical waste fluid collection and disposal system, a bone cement forming system, etc.

To further illustrate the apparatuses, systems and methods disclosed herein, the following non-limiting examples are provided:

Example 1 is an apparatus for applying a vacuum during a surgical procedure. The apparatus can optionally include a vacuum pump assembly having a port, a first housing, a second housing, a first silencer or tubular magnet and a second silencer. The first housing can define a first cavity receiving the vacuum pump assembly therein. A portion of the first housing can be formed by a portion of the port. The second housing can define a second cavity receiving the first housing therein. A portion of the second housing can be formed by a second portion of the port. The first silencer or tubular magnet can be coupled to the first housing and can have a longitudinal extent along a longitudinal axis. The first silencer or tubular magnet can extend from the first housing within the second cavity. The second silencer can be coupled to the second housing and can have a longitudinal extent along a longitudinal axis. The second silencer can extend from the second housing within second cavity.

Example 2 is the apparatus of Example 1, wherein first housing and the second housing can each be configured as a box enclosure and each can be formed of a same polymer material Example 3 is the apparatus of any one of Examples 1-2, wherein the first silencer or tubular magnet can be screwed into a first aperture in the first housing and the second silencer can be screwed into a second aperture in the second housing.

Example 4 is the apparatus of any one of Examples 1-3, optionally further comprising a plurality of mounts configured to couple the first housing to the second housing, wherein the plurality of mounts can be positioned on a first side of the first housing and on a second opposing side of the first housing.

Example 5 is the apparatus of any one of Examples 1-4, wherein the longitudinal axis of the first silencer or tubular magnet can be oriented substantially transverse to the longitudinal axis of the second silencer.

Example 6 is the apparatus of Example 5, wherein the first silencer or tubular magnet can be offset a distance from the second silencer in a direction that is substantially transverse to the longitudinal axis of the first silencer or tubular magnet and the longitudinal axis of the second silencer, and wherein the offset can be such that the longitudinal axis of the first silencer or tubular magnet does not intersect with the longitudinal axis of the second silencer.

Example 7 is the apparatus of any one of Examples 1-6, wherein the second silencer comprises a plurality of silencers.

Example 8 is a system for use during a surgical procedure, the system can optionally include a vacuum pump assembly, a first housing, a second housing a first silencer or tubular magnet and a second silencer. The first housing can define a first cavity configured to receive the vacuum pump assembly therein. The second housing can define a second cavity configured to receive the first housing therein. The first silencer or tubular magnet can be configured to couple to the first housing and can have a longitudinal extent along a longitudinal axis. The first silencer or tubular magnet. When coupled to the first housing extends outward from the first housing within the second cavity. The second silencer can be configured to couple to the second housing and can have a longitudinal extent along a longitudinal axis. The second silencer when coupled to the second housing extends inward from the second housing within second cavity. The longitudinal axis of the first silencer or tubular magnet can be arranged substantially transverse to the longitudinal axis of the second silencer when the first silencer or tubular magnet is coupled to the first housing and the second silencer is coupled to the second housing.

Example 9 is the system of Example 8, wherein a port of the vacuum pump assembly can form portions of or can be integrated with the first housing and the second housing.

Example 10 is the system of any one of Examples 8-9, wherein the first silencer or tubular magnet can be configured to be screwed into a first aperture in the first housing and the second silencer can be configured to be screwed into a second aperture in the second housing.

Example 11, is the system of any one of Examples 8-10, further comprising a plurality of mounts configured to couple the first housing to the second housing, wherein the plurality of mounts can be positioned on a first side of the first housing and on a second opposing side of the first housing.

Example 12 is the system of any one of Examples 8-11, wherein the first silencer or tubular magnet can be offset a distance from the second silencer in a direction that is substantially transverse to the longitudinal extent of the first silencer or tubular magnet and the longitudinal extent of the second silencer, and wherein the offset can be such that the longitudinal axis of the first silencer or tubular magnet does not intersect with the longitudinal axis of the second silencer.

Example 13 is the system of any one of Examples 8-12, wherein at least the second silencer comprises a plurality of silencers.

Example 14 is the system of any one of Examples 8-13, wherein first housing and the second housing can each be configured as a box enclosure and are each formed of a same polymer material.

Example 15 is a method for reducing noise during a surgical procedure, the noise resulting from operation of a vacuum pump. The method can optionally comprise positioning an assembly including the vacuum pump within the surgical suite. The assembly can include a first housing, a first silencer or tubular magnet, a second housing and a second silencer. The first housing can have a cavity receiving the vacuum pump. The first silencer or tubular magnet can be mounted to the first housing. The second housing can have a second cavity receiving the first housing. The first housing can be mounted within the second housing by a plurality of mounts configured to couple the first housing to the second housing. The plurality of mounts can be positioned on a first side of the first housing and on a second opposing side of the first housing. The second silencer can be mounted to the second housing and can extend with a longitudinal axis positioned substantially transverse to a longitudinal axis of the first silencer or tubular magnet.

Example 16 is the method of Example 15, further optionally comprising passing air through an inlet of the vacuum pump that forms portions of the first housing and the second housing as the first housing and the second housing are molded around the inlet.

Example 17 is the method of any one of Examples 15-16, wherein the first silencer or tubular magnet can be offset a distance from the second silencer in a direction that is substantially transverse to the longitudinal extent of the first silencer or tubular magnet and the longitudinal extent of the second silencer.

Example 18 is the method of any one of Examples 15-17, wherein the second silencer comprises a plurality of silencers.

Example 19 is any one or combination of features or elements of the Examples 1-18.

These and other examples and features of the present apparatuses, and systems will be set forth in part in the following Detailed Description. This Overview is intended to provide non-limiting examples of the present subject matter it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to apparatuses, systems and methods for housing and reducing noise of a vacuum pump that can be used during an orthopedic or other medical procedure.

Figure 1:
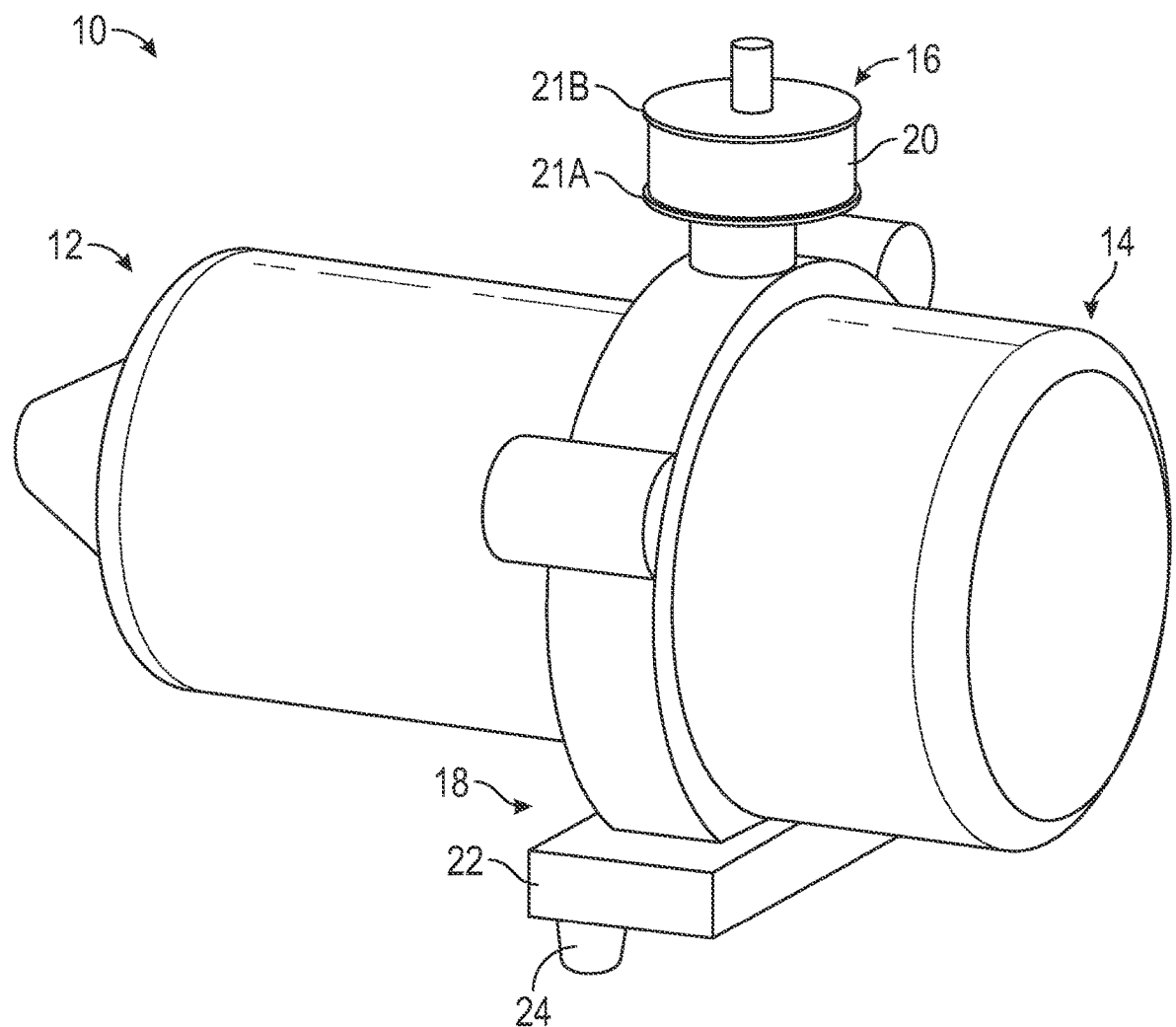
FIG. 1 is a perspective view of a vacuum pump assembly, in accordance with an example of the present disclosure.

FIG. 1 shows a perspective view of a vacuum pump assembly 10 according to an example of the present application. The vacuum pump assembly 10 can include a motor section 12, a pumping mechanism section 14, a port section 16 and a mount section 18.

The vacuum pump assembly 10 can have a housing the encloses at least the motor section 12 and the pumping mechanism section 14. The motor section 12 can be operatively coupled with the pumping mechanism section 14. The port section 16 can be coupled to the pumping mechanism section 14 and can be configured to allow gas or other type of fluid to communicate with internal components of the pumping mechanism section 14. The mount section 18 can be coupled to one or both of the motor section 12 and the pumping mechanism section 14.

According to one example, the port section 16 can comprise an inlet to the pumping mechanism section 14 allowing for the inflow of gas or other fluid. Although not illustrated in FIG. 1, according to some examples the vacuum pump assembly 10 can have an outlet that can be constructed in a similar manner to that of the port section 16. As shown in FIG. 1, the port section 16 can include a housing section 20 having a first lip feature 21A and a second lip feature 21B. The housing section 20 can be a flared or otherwise configured to comprise part of a first housing and a second housing of the assembly later described. As will be illustrated subsequently, the first lip feature 21A can be configured to be engaged by the first housing and the second lip feature 213 can be configured to be engaged by the second housing. The first lip feature 21A can be spaced from the second lip feature 21B. As discussed subsequently, the remainder of the vacuum pump assembly 10 can be connected to the port section 16 after insertion into the first housing, for example.

The motor section 12 can include an electric motor or another device configured to drive a pumping mechanism housed in the pumping mechanism section 14. The vacuum pump assembly 10 can be configured in a known manner. The vacuum pump assembly 10 can thus be configured as a gas transfer pump using kinetic transfer or positive displacement. The pumping mechanism can comprise any device known in the art such as a centrifugal pump, liquid ring vacuum pump rotary screw, rotary claw, side channel blower, etc.

The mount section 18 can be part of the housing that forms the motor section 12 and/or the pumping mechanism section 14. The mount section 18 can include a base portion 22 and feet 24. The feet 24 can be coupled to and extend from the base portion 22. The feet 24 can be configured to support the vacuum pump assembly 10.

Figure 2:
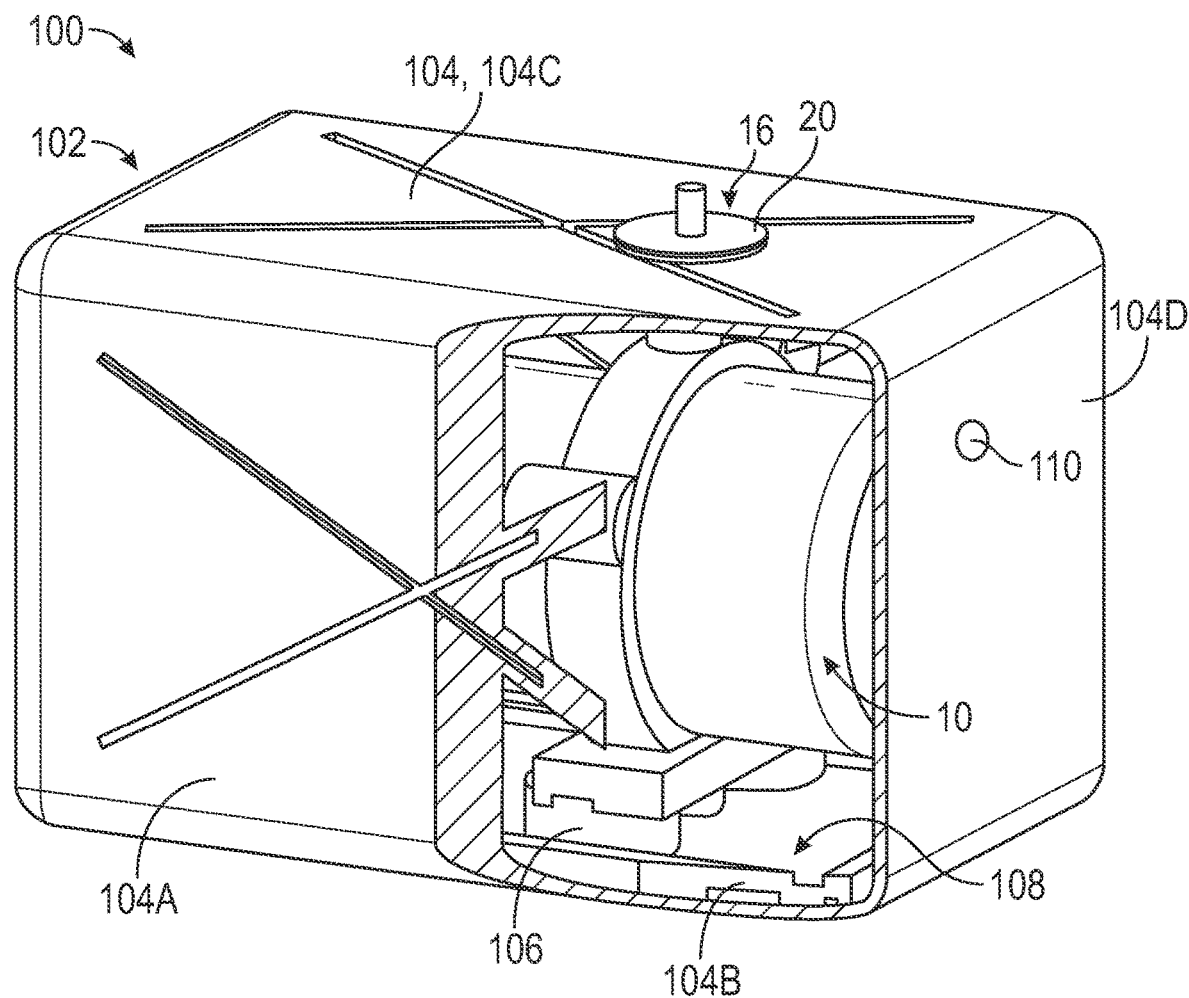
FIG. 2 is a partial cross-sectional view of a first containment apparatus used to house the vacuum pump assembly of FIG. 1, in accordance with an example of the present disclosure.

FIG. 2 shows a portion of an assembly 100 including a first housing 102 with a portion of a first wall 104A removed to show the vacuum pump assembly 10 therein according to an example of the present application. The first housing 102 (also referred to as a first containment apparatus or first box herein) can include a plurality of walls 104 including the first wall 104A, a second wall 104B, a third wall 104C, and a fourth wall 104D and one or more mounting features 106.

The first housing 102 can be configured as a box so as to form an enclosure that defines an interior cavity 108. To this end, the plurality of walls 104 can be connected together to form a rectangular or other shaped structure. Thus, the first wall 104A can be connected with the second wall 104B, the third wall 104C, the fourth wall 104D and additional walls. The second wall 104B can oppose the third wall 104C, One or more of the plurality of walls 104 can be removable from the others for insertion and removal of the vacuum pump assembly 10.

The interior cavity 108 can be configured to receive the vacuum pump assembly 10 as shown in FIG. 2. The one or more mounting features 106 can comprise projections or other features extending from the second wall 104B within the interior cavity 108. The one or more mounting features 106 can be configured to support the mount section 18 such as by receiving the feet 24 (FIG. 1) of the vacuum pump assembly 10.

According to the example of FIG. 2, the first housing 102 can also be partially formed by and/or can be in engagement with the port section 16, and in particular, the housing section 20 thereof. Such engagement/configuration can support the vacuum pump assembly 10 within the interior cavity 108 of the first housing 102. In particular, the third wall 104C of the first housing 102 can be molded or otherwise formed around the housing section 20 so as to engage the first lip feature 21A (FIG. 1). As such, the first housing 102, in particular the third wall 104C, can be formed with an aperture (not shown) or other feature configured to receive or engage the port section 16.

The fourth wall 104D can include one or more apertures 110 or other features configured to facilitate coupling of a first silencer with the first housing 102 as further described herein. The one or more apertures 110 can each comprise a threaded aperture, for example, designed to couple with threads of the first silencer. The one or more apertures 110 can extend fully through the fourth wall 104D so as to allow for communication with the interior cavity 108.

The first housing 102 can be formed of a polymer material, a composite material, a metal or metal alloy material, for example, According to some examples, the material can be polypropylene, polyethylene, polycarbonate, Acrylonitrile Butadiene Styrene (ABS), polyimide or blends of two or more polymers thereof. According to one example, the first housing 102 can be formed as a composite of polyimide and a fiber to support a weight of the vacuum pump assembly 10. Although not illustrated in FIG. 2, portions of the plurality of walls 104 that form the interior cavity 108 can be lined with a noise damping material such as noise dampening foam or other material(s).

Figure 3:
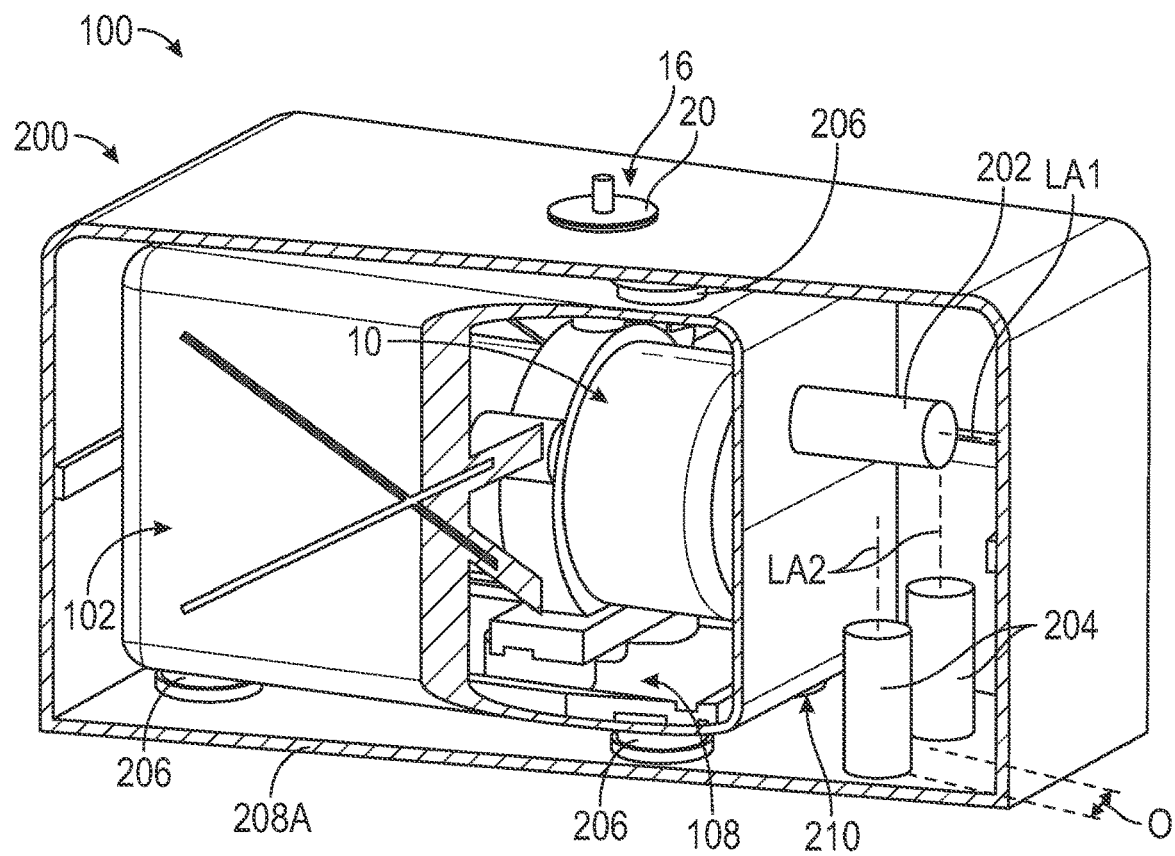
FIG. 3 is a partial cross-sectional view of a second containment apparatus used to house the first containment apparatus and the vacuum pump assembly of FIG. 1, in accordance with an example of the present disclosure.

FIG. 3 shows the assembly 100 including a second housing 200, a first silencer 202, at least a second silencer 204, the first housing 102 and the vacuum pump assembly 10. FIG. 3 shows a portion of the second housing 200 removed to illustrate the components of the assembly 100. It is contemplated that additional components such as electronics, power supply and connection components, etc. such as an electrical power unit 300 (FIG. 5) can be housed within the second housing 200, although the components are not specifically illustrated in FIG. 3.

Figure 5:
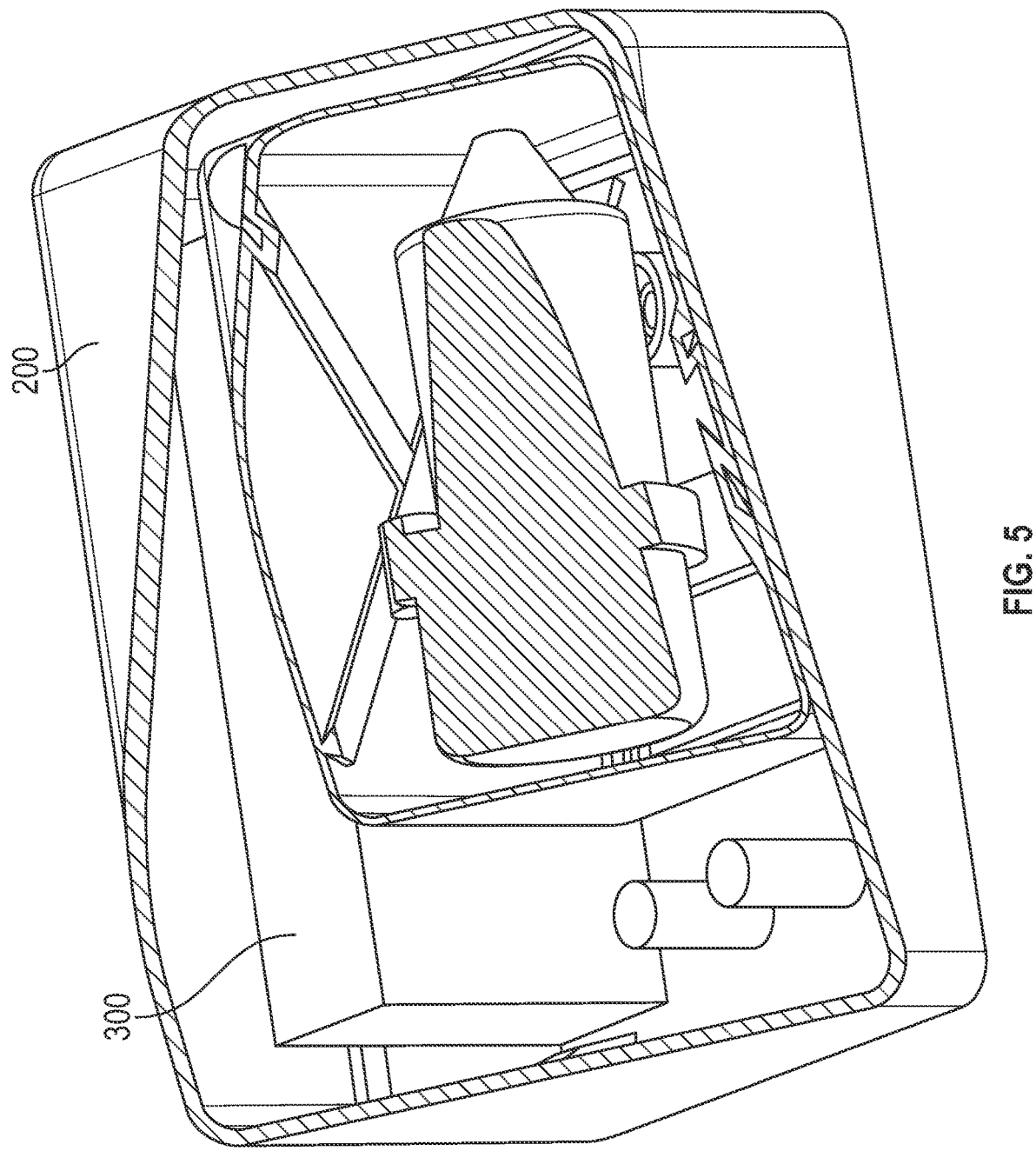
FIG. 5 is a partial cross-sectional view of the vacuum pump assembly and first and the second containment apparatuses showing an electrical power unit for the vacuum pump assembly positioned within the second containment apparatus.

As shown in FIG. 3, the second housing 200 can be configured to receive the first housing 102 and the vacuum pump assembly 10 therein. The second housing 200 can also be configured to receive the electrical power unit 300 for the vacuum pump assembly 10 as shown in FIG. 5. The second housing 200 can include a plurality of mounting features 206. The second housing 200 (also referred to as a second containment apparatus or second box herein) can additionally include a plurality of walls 208 including a first wall 208A and an opposing second wall 208B.

The second housing 200 can be configured as a box so as to form an enclosure that defines a second interior cavity 210. To this end, the plurality of walls 208 can be connected together to form a rectangular or other shaped structure. One or more of the plurality of walls 208 can be removable from the others for insertion and removal of first housing 102 (containing the vacuum pump assembly 10) and for insertion and removal of the additional components not specifically illustrated.

The second interior cavity 210 can be configured to receive the first housing 102 as shown in FIG. 3. The one or more mounting features 206 can comprise projections, blocks or other features extending from the second wall 208B within the second interior cavity 210. The one or more mounting features 206 can polymer material (e.g., rubber, foam, etc.) and be configured to support the first housing 102 such as by facilitating engagement between the first housing 102 and the second housing 200. The one or more mounting features 206 can be positioned on opposing sides of the second interior cavity 210 such as extending from the first wall 208A and the second wall 208B. In this arrangement, the one or more mounting features 206 can engage with opposing sides of the first housing 102.

According to the example of FIG. 3, the second housing 200 can also be partially formed by and/or can be in engagement with the port section 16, and in particular, the housing section 20 thereof. Such engagement/configuration can support/anchor the first housing 102 and the vacuum pump assembly 10 within the second interior cavity 210 of the second housing 200. In particular, the first wall 208A of the second housing 200 can be molded, integrated with or otherwise formed around the housing section 20 so as to engage the second lip feature 21B (FIG. 1). As such, the second housing 200, in particular the second wall 208B, can be formed with an aperture (not shown) or other feature configured to receive or engage the port section 16. It should be noted that in some example the port section 16 can remain connected with the first housing 102 and the second housing 200 even if a remainder of the vacuum pump assembly 10 is removed from therefrom.

The first wall 208A can include one or more apertures (not shown) or other features configured to facilitate coupling of the second silencer 204 with the second housing 200. The one or more apertures can be configured in the manner of the one or more apertures 110 previously shown in FIG. 2. Thus, the one or more apertures can each comprise a threaded aperture, for example, designed to couple with threads of the second silencer 204. The one or more apertures can extend fully through the first wall 208A so as to allow for communication with an exterior of the second housing 200.

The second housing 200 can be formed of a polymer material, a, composite material, a metal or metal alloy material, for example. The second housing 200 can be formed of a polymer material, a composite material, a metal or metal alloy material, for example. According to some examples, the material can be polypropylene, polyethylene, polycarbonate, Acrylonitrile Butadiene Styrene (ABS), polyimide or blends of two or more polymers thereof. According to one example, the second housing can be formed of a blend of ABS and polycarbonate for aesthetics and good shock absorption. Indeed, according to some examples the second housing 200 can be fabricated of a same polymer material as the first housing 102. According to one example Although not illustrated in FIG. 3, portions of the plurality of walls 208 that form the second interior cavity 210 can be lined with a noise damping material such as noise dampening foam or other material(s).

FIG. 3 also shows an exemplary arrangement of first silencer 202 and the at least one second silencer 204. As shown in the example of FIG. 3, the first silencer 202 can be coupled to the first housing 102 such as via the at least one aperture 110 (FIG. 2). Such coupling can be via treading, friction fit, snap fit or other mechanical means as known in the art. The first silencer 202 can have a longitudinal extent along a longitudinal axis $LA_1$. The first silencer 202 can be arranged with the longitudinal axis $LA_1$ that can be generally transverse to the fourth wall 104D of the first housing 102. Thus, the first silencer 202 can extend from the first housing 102 within the second interior cavity 210.

The at least one the second silencer 204 can include two or more silencers according to the example of FIG. 3. The second silencer 204 can be coupled to the second housing 200 such as via the one or more apertures previously described such as by treading, friction fit, snap fit or other mechanical means as known in the art. The second silencer 204 can be constructed in the same manner as the first silencer 202. Thus, second silencer 204 can have a longitudinal extent along a longitudinal axis $LA_2$. The second silencer 204 can be arranged with the longitudinal axis $LA_2$ that can be generally transverse to the first wall 208A of the second housing 200. Thus, the second silencer 204 can extend from the second housing 200 within the second interior cavity 210.

According to the example of FIG. 3, the longitudinal axis $LA_1$ of the first silencer 202 can be oriented substantially transverse to the longitudinal axis $LA_2$ of the second silencer 204 as measured in at least a first direction. The first silencer 202 can be offset as distance O from the second silencer 204 in a second direction that is substantially transverse to the longitudinal axis $LA_1$ of the first silencer 202 and the longitudinal axis $LA_2$ of the second silencer 204. The second direction can be substantially transverse to the first direction, for example. The offset O can be such that the longitudinal axis $LA_1$ of the first silencer 202 does not intersect with the longitudinal axis $LA_2$ of the second silencer 204. It should be noted that although a single first silencer 202 is illustrated in FIG. 3, according to other examples, the first silencer 202 can be a plurality of silencers as is the case with the second silencer 204.

Figure 4:
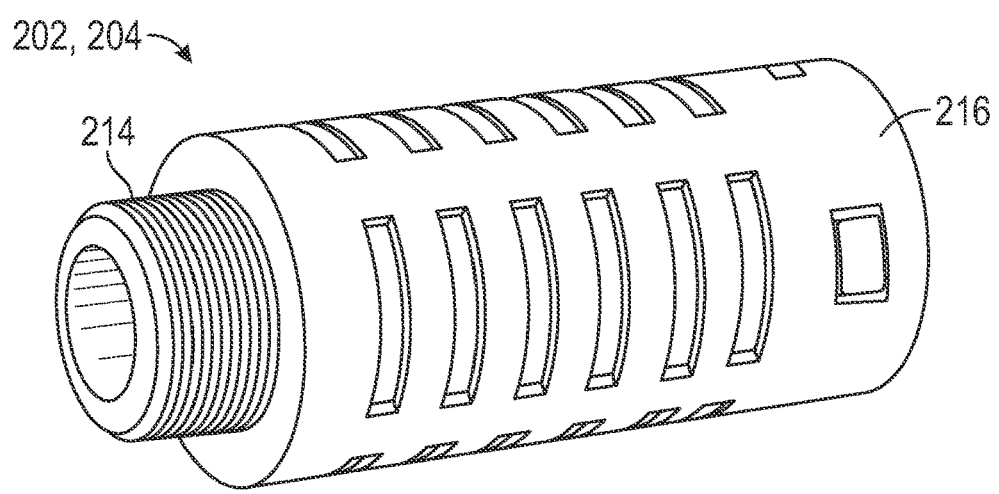
FIG. 4 is a perspective view of an example of a silencer apparatus that can be utilized with the present application.

FIG. 4 shows an example of one of the first silencer 202 or the second silencer 204. The silencer 202, 204 can include a base portion 214 and a body portion 216. The silencer 202, 204 can be configured in a manner known in art and can be manufactured by Coval® such as component number SILGV10M5F. As discussed previously, the base portion 214 can be configured to thread or otherwise couple with a mating feature of the first housing or second housing. The body portion 216 can be coupled to the base portion 214 and can be hollow with an outer housing of polymer or other material. A plurality of ports can be formed in the body portion 216. An interior of the body portion 216 can be lined or filled with an acoustic fiber such as a carbon fiber. The base portion 214 can be hollow and configured to communicate via a passageway with the hollow interior of the body portion 216. With this construction of the base portion 214, the silencer 202, 204 can be configured to communicate from within the interior of the first housing or exterior of the second housing to the second interior cavity 210 (FIG. 3) defined by the second housing 200.

Figure 6:
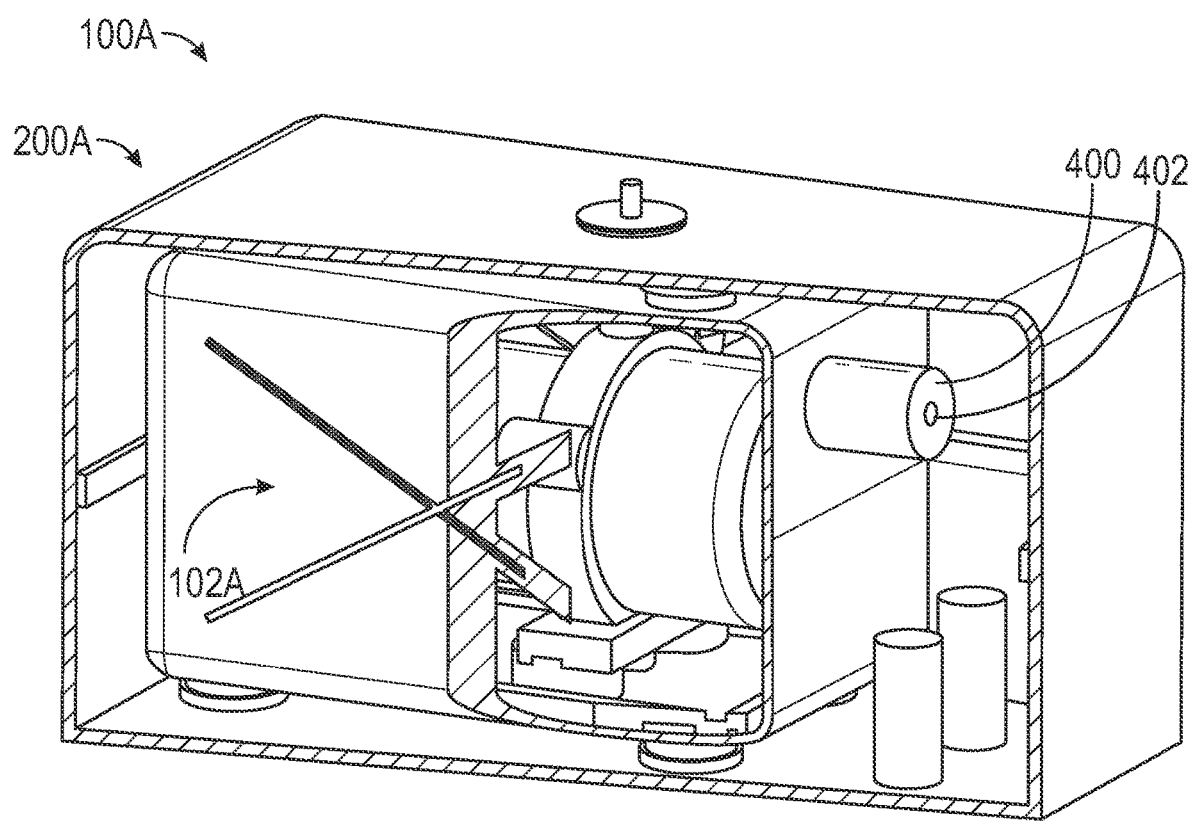
FIG. 6 shows another example of containment apparatuses and the vacuum pump assembly with a tubular magnet, according to another example of the present disclosure.

FIG. 6 shows an assembly 100A according to another example. The assembly 100A can be configured in the manner of the assembly 100 as previously described save that the first silencer 202 can be replaced by a tubular magnet 400. This tubular magnet 400 can be positioned within a second housing 200A and can have a passage 402 therethrough that communicates with the interior of a first housing 102A. The tubular magnet 400 can be configured to catch iron or other ferrous particles carried by air passing through the tubular magnet 400 passage 402 between the first housing 102A and the second housing 200A It is contemplated that the tubular magnet 400 can be arranged and positioned in the manner of the first silencer 202 as previously discussed. Thus, the tubular magnet 400 can have a longitudinal axis that aligns with the passage 402. The tubular magnet 400 can be offset from the second one or more silencers as illustrated and previously discussed. It is contemplated that the tubular magnet 400 can be used in combination with the first silencer (FIG. 3) rather than replacing it. It is also contemplated that one or more of the second silencers (204 in FIG. 3) could be replaced by one or more tubular magnet(s) 400.

Additional Notes

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The above detailed description includes references to the accompanying drawings, which form a part of the detailed description. The drawings show, by way of illustration, specific embodiments in which the invention can be practiced. These embodiments are also referred to herein as "examples," Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An apparatus for applying a vacuum during a surgical procedure, the apparatus comprising:
   a vacuum pump assembly including a port;
   a first housing defining a first cavity receiving the vacuum pump assembly therein, a portion of the first housing formed by a portion of the port;
   a second housing defining a second cavity receiving the first housing therein, wherein a portion of the second housing is formed by a second portion of the port;
   a first silencer or a tubular magnet coupled to the first housing and having a longitudinal extent along a longitudinal axis, wherein the first silencer or tubular magnet is screwed into a first aperture in the first housing with a first threaded section located at a first longitudinal end portion, wherein the first silencer or tubular magnet extends from the first housing within the second cavity along the longitudinal axis, and wherein the first silencer or tubular magnet is contacted only at the first longitudinal end portion thereof; and
   a second silencer coupled to the second housing and having a longitudinal extent along a longitudinal axis, wherein the second silencer is screwed into a second aperture in the second housing with a second threaded section located at a second longitudinal end portion, wherein the second silencer extends from the second housing toward the first silencer or tubular magnet within the second cavity, and wherein the second silencer is contacted only at the second longitudinal end portion thereof.

2. The apparatus of claim 1, wherein first housing and the second housing are each configured as a box enclosure and are each formed of a same polymer material.

3. The apparatus of claim 1, further comprising a plurality of mounts configured to couple the first housing to the second housing, wherein the plurality of mounts are positioned on a first side of the first housing and on a second opposing side of the first housing.

4. The apparatus of claim 1, wherein the longitudinal axis of the first silencer is oriented substantially transverse to the longitudinal axis of the second silencer.

5. The apparatus of claim 4, wherein the first silencer or tubular magnet is offset a distance from the second silencer in a direction that is substantially transverse to the longitudinal axis of the first silencer or tubular magnet and the longitudinal axis of the second silencer, and wherein the offset is such that the longitudinal axis of the first silencer or tubular magnet does not intersect with the longitudinal axis of the second silencer.

6. The apparatus of claim 1, wherein the second silencer comprises a plurality of silencers.

7. A system for use during a surgical procedure, the system comprising:
   a vacuum pump assembly;
   a first housing defining a first cavity configured to receive the vacuum pump assembly therein;
   a second housing defining a second cavity configured to receive the first housing therein;

a first silencer or tubular magnet configured to couple to the first housing and having a longitudinal extent along a longitudinal axis, wherein the first silencer or tubular magnet is screwed into a first aperture in the first housing with a first threaded section located at a first longitudinal end portion, wherein the first silencer or tubular magnet when coupled to the first housing extends outward from the first housing within the second cavity along the longitudinal axis, and wherein the first silencer or tubular magnet is contacted only at the first longitudinal end portion thereof; and a second silencer configured to couple to the second housing and having a longitudinal extent along a longitudinal axis, wherein the second silencer is screwed into a second aperture in the second housing with a second threaded section located at a second longitudinal end portion, wherein the second silencer, when coupled to the second housing, extends inward from the second housing toward the first silencer or tubular magnet within the second cavity, wherein the second silencer is contacted only at the second longitudinal end portion thereof, and wherein the longitudinal axis of the first silencer or tubular magnet is substantially transverse to the longitudinal axis of the second silencer when the first silencer or tubular magnet is coupled to the first housing and the second silencer is coupled to the second housing.

8. The system of claim 7, wherein a port of the vacuum pump assembly forms portions of or are integrated with the first housing and the second housing.

9. The system of claim 7, further comprising a plurality of mounts configured to couple the first housing to the second housing, wherein the plurality of mounts are positioned on a first side of the first housing and on a second opposing side of the first housing.

10. The system of claim 7, wherein the second silencer is offset a distance from the first silencer or tubular magnet in a direction that is substantially transverse to the longitudinal extent of the first silencer or the tubular magnet and the longitudinal extent of the second silencer, and wherein the offset is such that the longitudinal axis of the first silencer or tubular magnet does not intersect with the longitudinal axis of the second silencer.

11. The system of claim 7, wherein at least the second silencer comprises a plurality of silencers.

12. The system of claim 7, wherein first housing and the second housing are each configured as a box enclosure and are each formed of a same polymer material.

13. A method for reducing noise during a surgical procedure, the noise resulting from operation of a vacuum pump, the method comprising: positioning an assembly including the vacuum pump within a surgical suite, the assembly comprising: a first housing having a cavity receiving the vacuum pump; a first silencer or tubular magnet mounted to the first housing only at a first end portion thereof, a second housing having a second cavity receiving the first housing, wherein the first housing is mounted within the second housing by a plurality of mounts configured to couple the first housing to the second housing, wherein the plurality of mounts are positioned on a first side of the first housing and on a second opposing side of the first housing; and a second silencer mounted to the second housing only at a second end portion thereof and extending with a longitudinal axis positioned substantially transverse to a longitudinal axis of the first silencer or the tubular magnet, wherein the second silencer extends from the second end portion toward the first silencer; wherein the first silencer or tubular magnet is contacted only at the first end portion and the second silencer is contacted only at the second end portion such that the first silencer or tubular magnet and the second silencer freely extend within the second cavity.

14. The method of claim 13, further comprising passing air through an inlet of the vacuum pump that forms portions of the first housing and the second housing as the first housing and the second housing are molded around the inlet.

15. The method of claim 13, wherein the second silencer is offset a distance from the first silencer or tubular magnet in a direction that is substantially transverse to a longitudinal extent of the first silencer or tubular magnet and the longitudinal extent of the second silencer.

16. The method of claim 13, wherein the second silencer comprises a plurality of silencers.

\* \* \* \* \*